(12) United States Patent
Hunt et al.

(10) Patent No.: US 9,557,267 B2
(45) Date of Patent: Jan. 31, 2017

(54) TERAHERTZ IMAGING VIA SIMULTANEOUS SURFACE AND SUB-SURFACE EVALUATION VIA NON-LINEAR OPTICAL RESPONSE

(71) Applicant: The Boeing Company, Huntington Beach, CA (US)

(72) Inventors: Jeffrey H. Hunt, Thousand Oaks, CA (US); John H. Belk, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 161 days.

(21) Appl. No.: 14/520,761

(22) Filed: Oct. 22, 2014

(65) Prior Publication Data

US 2016/0116406 A1  Apr. 28, 2016

(51) Int. Cl.
 *G01N 21/63* (2006.01)
 *G01N 21/3581* (2014.01)

(52) U.S. Cl.
 CPC ........ *G01N 21/636* (2013.01); *G01N 21/3581* (2013.01)

(58) Field of Classification Search
 CPC .............................. G01N 21/55; G01N 21/47
 USPC ....................................................... 250/341.1
 See application file for complete search history.

(56) References Cited

U.S. PATENT DOCUMENTS

| | | | | |
|---|---|---|---|---|
| 6,563,622 B2* | 5/2003 | Mueller | ............... | G02F 1/3534 398/115 |
| 7,304,305 B2 | 12/2007 | Hunt | | |
| 8,416,408 B1* | 4/2013 | Herzinger | ............... | G01J 4/04 356/364 |
| 8,736,838 B2 | 5/2014 | Herzinger | | |
| 8,743,368 B2 | 6/2014 | Meyers et al. | | |
| 2003/0231302 A1* | 12/2003 | Hunt | ............... | G01N 21/9501 356/237.2 |
| 2003/0234360 A1* | 12/2003 | Hunt | ............... | G01N 21/3563 250/339.06 |
| 2003/0234925 A1* | 12/2003 | Hunt | ............... | G01J 11/00 356/237.1 |
| 2003/0234927 A1* | 12/2003 | Hunt | ............... | G01N 21/17 356/237.2 |
| 2003/0235381 A1* | 12/2003 | Hunt | ............... | G01N 21/17 385/122 |
| 2005/0098728 A1* | 5/2005 | Alfano | ............... | G01N 21/3581 250/341.8 |
| 2008/0203306 A1* | 8/2008 | Zhang | ............... | G01J 3/42 250/341.1 |
| 2011/0037001 A1* | 2/2011 | Maki | ............... | H01Q 3/42 250/503.1 |
| 2012/0261580 A1* | 10/2012 | Herzinger | ............... | G01J 4/04 250/353 |

(Continued)

OTHER PUBLICATIONS

ODA, "Uncooled Bolometer-type Terahertz Focal Plane Array and Camera for Real-Time Imaging," C.R. Physique, vol. 11, 2010, pp. 496-509.

*Primary Examiner* — David Porta
*Assistant Examiner* — Gisselle Gutierrez (57) ABSTRACT

Methods, systems and apparatuses are disclosed for interrogating characteristics of a substrate material surface and sub-surface by evaluating: 1) sum frequency output beams produced by combining an optical source input and a Terahertz source input, and 2) Terahertz second harmonic frequency output from a Terahertz source input.

17 Claims, 5 Drawing Sheets

(56) References Cited

U.S. PATENT DOCUMENTS

| | | | | |
|---|---|---|---|---|
| 2013/0026368 A1* | 1/2013 | Herzinger | ............... | G01J 4/04 |
| | | | | 250/341.3 |
| 2013/0147363 A1* | 6/2013 | Hunt | ............... | H04B 10/116 |
| | | | | 315/137 |
| 2013/0161541 A1* | 6/2013 | Kim | ............... | G02F 2/002 |
| | | | | 250/504 R |
| 2014/0061474 A1* | 3/2014 | Kitamura | ............... | G01J 3/42 |
| | | | | 250/339.02 |
| 2014/0299773 A1* | 10/2014 | Nawata | ............... | G01J 1/0425 |
| | | | | 250/339.06 |
| 2015/0316475 A1* | 11/2015 | Rahman | ............... | G01N 21/9501 |
| | | | | 250/339.02 |
| 2016/0116396 A1* | 4/2016 | Hunt | ............... | G01N 21/211 |
| | | | | 356/369 |
| 2016/0116400 A1* | 4/2016 | Hunt | ............... | G01N 21/3581 |
| | | | | 250/341.1 |
| 2016/0116401 A1* | 4/2016 | Hunt | ............... | G01N 21/3581 |
| | | | | 250/339.02 |

\* cited by examiner

TERAHERTZ IMAGING VIA SIMULTANEOUS SURFACE AND SUB-SURFACE EVALUATION VIA NON-LINEAR OPTICAL RESPONSE

TECHNOLOGICAL FIELD

The present disclosure relates to monitoring material surfaces and sub-surfaces. More particularly the present disclosure relates to monitoring material surfaces using second-order non-linear optics to achieve Terahertz level material evaluation and characterization.

BACKGROUND

In non-linear optical, or wave mixing processes, outputs are produced at sum, difference or harmonic frequencies of the input(s). Second order non-linear optics, or three wave mixing involves combining two inputs to produce one output at one of the combined frequencies. The use of second order non-linear optical surface spectroscopy to examine physical properties of a material surface is known. However, practical constraints on such known methods have impeded progress on the material evaluation and characterization beneath the surface of a material under inspection.

The Terahertz (hereinafter "THz") range refers to electromagnetic waves with frequencies between 100 GHz and 10 THz, or wavelengths between 3 mm and 30 µm, existing in the radiation spectrum between the microwave and infrared region. Terahertz waves are known to pass through a variety of amorphous and opaque substances. In addition, many biomolecules, proteins, explosives or narcotics also feature characteristic absorption lines, so-called spectral "fingerprints", at frequencies between 0.1 and 2 THz. The two main advantages of THz radiation are thus the penetration of conventionally opaque materials on one hand, and a high chemical selectivity on the other hand. Terahertz imaging is therefore thought to be a non-destructive technique for interrogating dielectric (non-conducting) materials. The use of THz waves for non-destructive evaluation of materials enables inspection of multi-layered structures and can therefore identify abnormalities from foreign material inclusions (contamination) delamination, heat damage, etc.

The spectroscopic frequency band of a 0.5 to 3 THz is not easily accessible. Electronic sources like Gunn or Schottky diodes with subsequent frequency multipliers, provide high output levels (mW range) up to some 100 GHz, yet become inefficient in the sub-millimeter range. Direct optical sources, like quantum cascade lasers, are usually limited to frequencies>5 THz, even when operated at cryogenic temperatures.

Optoelectronic THz generation is an expression for indirect methods, where near-infrared laser light illuminates a metal-semiconductor-metal structure, generating a photocurrent that becomes the source of a THz wave. Both pulsed and continuous-wave (CW) techniques have been realized, and both have their advantages and limitations. Pulsed THz radiation offers a higher bandwidth (typically from 0.1 to 5 THz) and permits very fast measurements; a spectrum can be acquired within milliseconds. On the other hand, the frequency resolution is limited to several GHz. Vice versa, a CW system features a somewhat lower bandwidth (typically about 0.1 to about 2 THz) and requires longer measurement times (acquiring a spectrum takes several minutes, yet the frequency can be controlled with extreme precision (down to single MHz).

Composite materials such as fiberglass, Kevlar and carbon fiber are increasingly being used as structural components in aircraft because of their high strength to weight ratios, improved performance, reduced corrosion, etc., compared with other known structural materials. However, composites can be weakened by various defects and stress during their life cycle. Further, routine maintenance of composites requires complicated inspection and repair techniques.

Terahertz (THz) radiation offers a non-invasive, non-contract, non-ionizing method of assessing composite part condition. However, the use of THz radiation diagnostic arrays presents difficulties. For example, to image a surface, THz diagnostic arrays require a focal plane array that can detect the output signal from the surface. However, known THz focal plane arrays have not shown the levels of resolution attained by optical systems.

SUMMARY

According to one aspect, the present disclosure is directed to a method for evaluating a substrate material including a substrate material surface. A first input beam of electromagnetic radiation is directed onto a predetermined area of a substrate material, the material having a substrate material surface and a substrate material sub-surface with the electromagnetic radiation of the first input beam having a wavelength of from about 1000 nm to about 300 nm. A second input beam of THz electromagnetic radiation is directed onto the predetermined area of the substrate material surface, with the electromagnetic radiation of the second input beam having a THz wavelength of from about 0.3 mm to about 3 microns. The first input beam and the second input beam are mixed at the substrate material surface to provide a sum frequency output beam. The second input beam penetrates the substrate material surface into the substrate material sub-surface to provide a THz second harmonic output beam comprising a THz second harmonic signal of the second input beam. The sum frequency output beam is directed to, received, collected and evaluated by a sum frequency output detector and the THz second harmonic output beam is received, collected and evaluated by a THz second harmonic output beam detector.

According to another aspect, one or more characteristics of the substrate material surface are measured based on the sum frequency output beam received by the sum frequency output beam detector. One or more characteristics of the substrate material surface and sub-surface are measured based on the THz second harmonic output beam directed to and received by the THz second harmonic output beam detector.

According to a still further aspect, the substrate material is substantially opaque to the first beam of electromagnetic radiation. According to the present specification "substantially opaque" refers to the substrate material property where very little, if any, input radiation is transmitted through the substrate material.

Still further, according to another aspect of the present disclosure, the second input beam penetrates into the substrate material subsurface to a depth of from about 100 microns to about 2 mm beneath the substrate material surface.

In another aspect, at least one of the first input beam and second input beam are each emitted from a laser.

In a still further aspect, at least one of the sum frequency output beam and the THz second harmonic output beam is non-co-linear with at least one of the first input beam and/or the second input beam.

In another aspect, the first input beam and the second input beam are directed onto a predetermined area of the substrate material simultaneously or substantially simultaneously. It is understood that pulsed lasers have a temporal duration of, typically about, one nanosecond or one picosecond. Therefore, according to aspects of this disclosure, "substantially simultaneously" refers to laser pulses arriving at a predetermined area or region on a substrate material surface, such that their pulses arrive at the substrate material surface in overlapping fashion, and the pulses are out of synch for only a duration of from about 50 to about 100 picoseconds.

In one aspect, the present disclosure is further directed to systems and apparatuses (including non-linear optical systems and apparatuses) for non-invasively evaluating surface and sub-surface characteristics of a substrate material. The system comprises a substrate material having a substrate material surface and a substrate material sub-surface, and at least one optical source, with the at least one optical source emitting an optical source input beam at a wavelength of from about 1000 nm to about 300 nm. The system further comprises at least one THz source, with the THz source emitting a THz source input beam at a wavelength of from about 0.3 mm to about 3.0 microns. At least one sum frequency output detector for detecting a sum frequency output produced from the combined optical source input and the THz source input is positioned at a location to receive sum frequency output beams, with the sum frequency output beams reflected from a predetermined area on the substrate material surface. At least one THz second harmonic frequency output detector for detecting THz second harmonic frequency output beams from the substrate material surface and the substrate material sub-surface is positioned at a location to receive THz second harmonic frequency output beams, with the THz second harmonic frequency output beams reflected from a predetermined area on the substrate material surface and substrate material sub-surface to the THz second harmonic frequency detector. The sum frequency output beam is reflected from the predetermined area on the substrate material surface and the substrate material sub-surface. The sum frequency output beam generates a signal directed to and received by the sum frequency detector, and the THz second harmonic frequency output beam is reflected from the predetermined area on the substrate material surface and substrate material sub-surface and generates a signal directed to and received by the THz second harmonic frequency detector, whereby one or more characteristics of the substrate material are measured by evaluating the sum frequency output beam directed to and received by the sum frequency output beam detector.

Each input beam is directed at a predetermined area on the substrate material surface. For purposes of the present disclosure, the terms "predetermined area", "area", "region" and "location", relative the substrate material surface and sub-surface are used interchangeably and have equivalent meaning.

For the purpose of this disclosure, the terms "interrogation" and "characterization" are used interchangeably and have equivalent meaning when referring to the substrate material.

For the purpose of this disclosure, the terms "characteristics" and "properties" are used interchangeably and have equivalent meaning when referring to the substrate material.

The THz source input beam penetrates the substrate material surface into the substrate material sub-surface to a desired depth from the substrate material surface. The input beam is combined at a predetermined area on the substrate material surface to produce a sum frequency output beam. The sum frequency output beam is reflected from the predetermined location on the substrate material surface and is received by the sum frequency output detector. The THz source input beam penetrates the substrate material surface to a predetermined depth and a THz second harmonic frequency output beam is produced. The THz second harmonic output beam is reflected from the substrate material surface and substrate material sub-surface to the THz second harmonic frequency output detector. The output beams are received by the detectors substantially simultaneously, with each output beam generating a signal. Features of the substrate material surface and substrate material sub-surface are characterized based on the characteristics of the sum frequency output beam received by the sum frequency output detector and the THz second harmonic frequency output beams received by the THz second harmonic frequency output beam detector.

In a further aspect, the optical source does not emit in the THz frequency range.

In a still further aspect, the optical source and the THz sources are lasers.

In another aspect, the THz source emits a THz input beam at a wavelength of from about 0.3 mm to about 3 microns.

In yet another aspect, the optical source having a frequency in the THz frequency range emits radiation that penetrates the substrate material surface.

In a still further aspect, the optical source having a frequency in the THz range emits radiation that penetrates the substrate material surface into the substrate material subsurface to a depth of from about 100 microns to about 2 mm beneath the substrate material surface.

In another aspect, at least one sum frequency detector receives a sum frequency output from the substrate material surface.

In a further aspect, at least one THz second harmonic frequency output detector receives a THz second harmonic frequency output from the substrate material surface and substrate material surface and sub-surface.

According to a still further aspect, at least one detector comprises software to characterize features of the substrate material based on the characteristics of the output beams from the substrate material received by the detector.

In a still further aspect, at least one detector generates a signal and sends the generated signal to a component comprising software to characterize features of the substrate material based on the characteristics of the output beams received by the detector.

In a still further aspect, at least one detector generates a signal and sends the generated signal to a remotely located component, said remotely located component comprising software to characterize features of the substrate material surface and substrate material sub-surface based on the characteristics of the output received by the detector.

In another aspect, the present disclosure is directed to apparatuses comprising the systems described above.

In a still further aspect, the methods, systems and apparatuses of the present disclosure are directed to a vehicle comprising a substrate material surface, wherein at least a portion of the substrate material surface is interrogated by directing a first input beam comprising electromagnetic radiation onto a predetermined area of a substrate material having a substrate material surface and a substrate material sub-surface. A second input beam comprising electromagnetic radiation is directed onto the predetermined area of the substrate material surface, the electromagnetic radiation of the second input beam having a THz wavelength between about 0.3 mm and about 3 microns. The first and second input beams are mixed at the substrate material surface to provide a sum frequency output beam. The second input beam penetrates the substrate material surface to a predetermined depth into the substrate material sub-surface to provide a THz second harmonic output beam comprising a THz second harmonic signal of the second harmonic beam. The sum frequency output beam is directed to and received by a sum frequency output beam detector. The THz second harmonic output beam is directed to and received by a TH$_Z$ second harmonic output beam detector. One or more characteristics of the substrate material is evaluated by measuring the sum frequency output beam received by the sum frequency output beam detector.

In a further aspect, the vehicle includes, but is not limited to, manned or unmanned objects and structures in an atmospheric or space environment. Contemplated objects include vehicles, such as, for example, aircraft, satellites, rockets, missiles, etc., and therefor include manned and unmanned aircraft, spacecraft, terrestrial vehicles, non-terrestrial vehicles and even surface and sub-surface water-borne marine vehicles, objects and structures.

The methods, systems and apparatuses of the present disclosure provide solutions to the problems of accurately and cost-effectively interrogating and evaluating substrate material surface and sub-surface characteristics including, but not limited to the interrogation and evaluation of chemical composition, homogeneity, heterogeneity, mechanical surface irregularities (including, but not limited to, defects and contamination), crystallographic defects, surface, etc., and combinations thereof.

BRIEF DESCRIPTION OF THE DRAWINGS

Having thus described variations of the disclosure in general terms, reference will now be made to the accompanying drawings, which are not necessarily drawn to scale, and wherein:

DETAILED DESCRIPTION

Scalable and repeatable non-invasive surface diagnostic techniques that can be applied in a manufacturing environment are rare and difficult to implement. It is even more difficult to employ such diagnostic techniques that can inspect a material sub-surface. Surface diagnostic methods using second order surface non-linear effects are known. Equally well-known is recognition that a signal will only be generated at a place where the signal can penetrate. Opaque materials such as, for example, composite materials are opaque at optical frequencies, while they are respond as being less opaque to radiation having longer wavelengths, such as the wavelengths found in the THz regime.

According to aspects of the present disclosure, THz imaging of a substrate surface and sub-surface is achieved by the substantially simultaneous interrogation of a substrate material surface and subsurface via non-linear optical response methods. The substrate materials are preferably opaque materials such as, for example, composite materials that are in the longer wavelength regions of the electromagnetic spectrum, such as the THz regime. The methods disclosed provide both, an optical source and a THz source, both sources emitting radiation at predetermined wavelengths that are directed to a predetermined area on a substrate material surface. The interaction of the two sources substantially simultaneously provides a signal from the surface at a sum frequency between the two sources. The THz input signal will penetrate to a predetermined depth below the substrate material surface, so that any material defects resulting from defect, contamination, etc. will be detectable in the second harmonic signal of the THz signal. According to one aspect of the disclosure, the THz input signal penetrates beneath a substrate material surface to a depth of from about 100 microns to about 1 mm. Since the optical source signal and the THz signal will be generated substantially simultaneously, the detection of the output signals provides a more accurate and complete assessment of the substrate material surface and subsurface than can be conducted by known inspection systems.

Aspects of this disclosure are further directed to methods, systems and apparatuses that substantially simultaneously apply, to a substrate material surface, combined sum frequency wavelengths from the THz and optical (non-THz source) spectral wavelength ranges. The long wavelength and relative transparency of non-metal materials, such as, for example, composites allow the evanescent wave at the THz frequency to penetrate beneath the surface of a substrate material. Meanwhile, the frequencies of the optical source will remain proximate to the substrate material surface (will not penetrate below the substrate material surface). As a result, the optical/THz sum frequency will provide diagnostic information only at the first few molecular layers of the substrate material surface. However, the THz second harmonic signal will probe below the substrate material surface to a predetermined depth on the order of the wavelength.

The source responsible for the DFG is the non-linear polarization P$^{(2)}$ in the medium.

$$\vec{P}^{(2)}(\omega_{THz}=\omega_1-\omega_2)=\vec{\chi}^{(2)}(\omega_{THz}):\vec{E}(\omega_1)\vec{E}(\omega_2).$$

If the medium has an inversion symmetry, then the non-linear susceptibility $\vec{\chi}^{(2)}$ vanishes in the electric-dipole approximation. Since the inversion symmetry is necessarily broken at an interface, this makes DFG an effective surface probe. For a monolayer of molecules at a surface, the surface nonlinear susceptibility is typically ~$10^{-15}$ esu, which should yield a signal of $10^3$ photons/pulse with a laser pulse of 10 milliJoule energy and 10 nsec duration impinging on a surface area of 0.2 cm$^2$.

Figure 1:
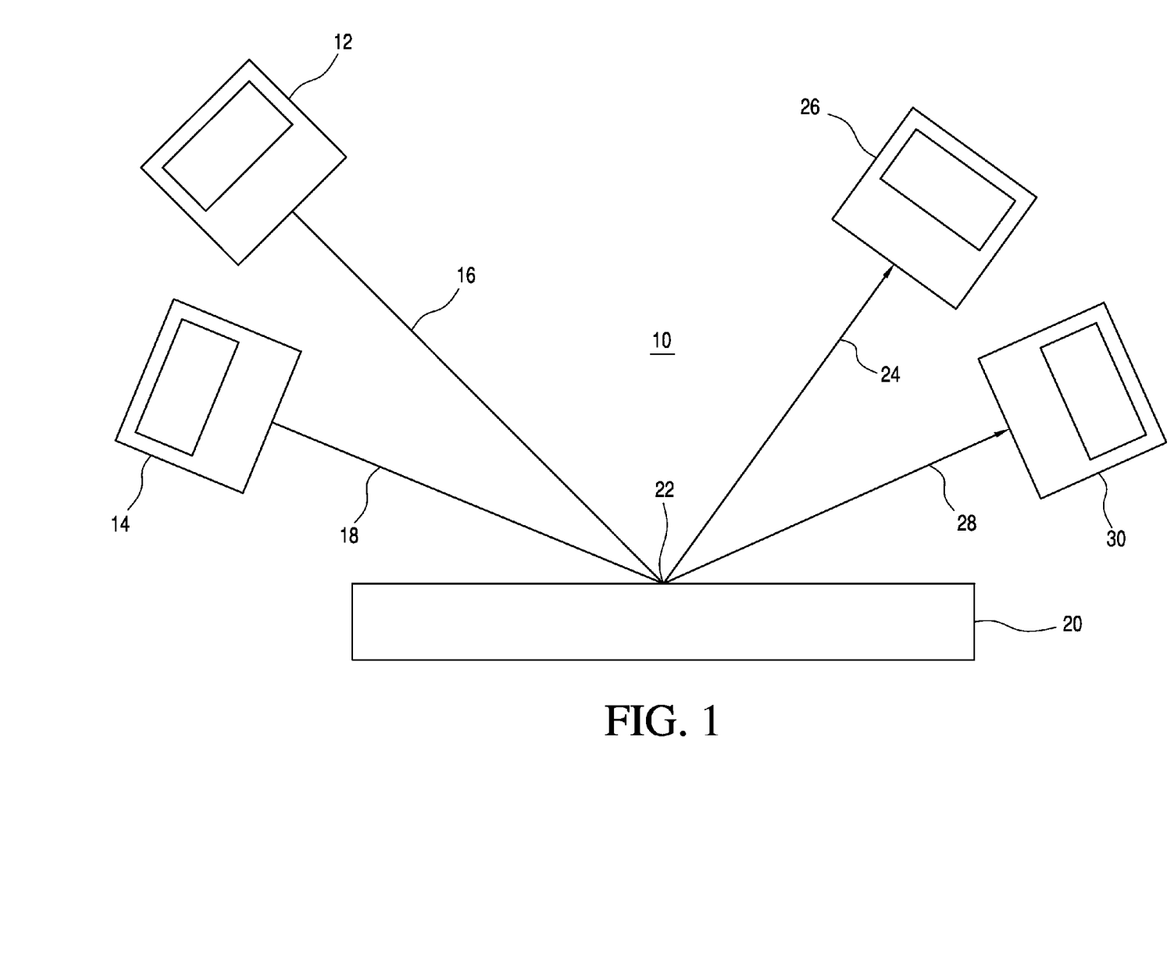
FIG. 1 is a schematic diagram of one aspect of the present disclosure.
Figure 3:
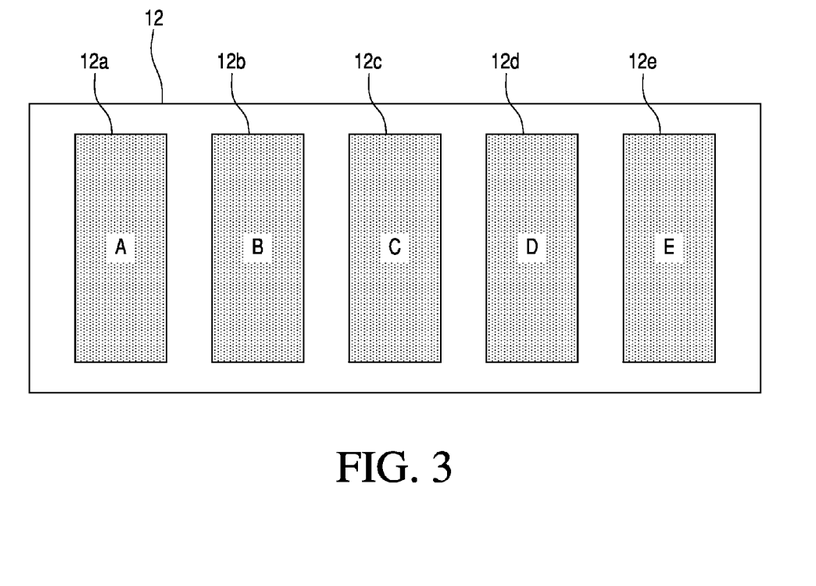
FIG. 3 is a schematic diagram of a variation of the present disclosure.
Figure 4:
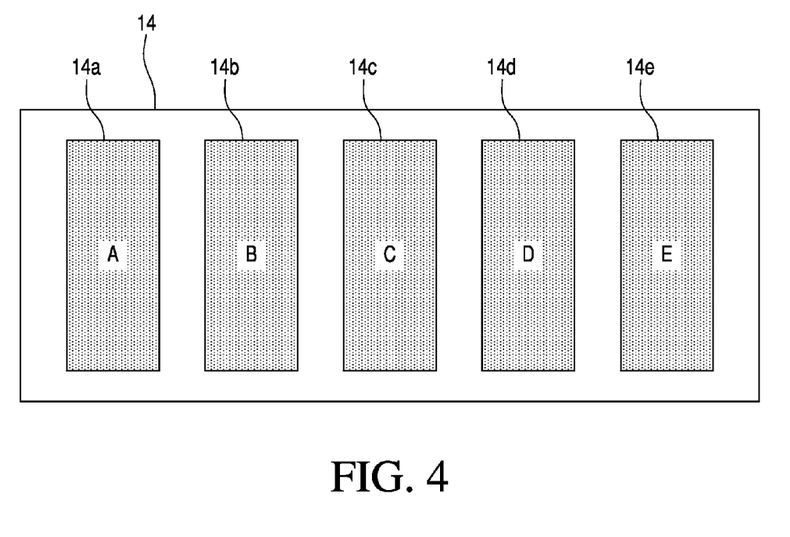
FIG. 4 is a schematic diagram of a variation of the present disclosure.

FIG. 1 shows a schematic representation of one aspect of the present disclosure. Diagnostic system 10 shows an optical source 12 and a THz source 14. As shown in FIG. 3, optical source 12 comprises: an optical source of electromagnetic radiation in the optical regime 12a; optical elements for regulation and control of radiation intensity 12b; optical elements for control of radiation polarization 12c; optical elements for control of radiation bandwidth 12d; and optical elements for control of the manner of radiation propagation, such as, for example, lenses 12e. It is understood that the elements 12a-12e are illustrative and that the order and location in which they are positioned within optical source 12 is not meant to be restrictive in any way. As shown in FIG. 4, THz source 14 comprises: a source of electromagnetic radiation in the THz regime 14a; elements for regulation and control of radiation intensity 14b; elements for control of radiation polarization 14c; elements for control of radiation bandwidth 14d; and elements for control of the manner of radiation propagation, such as, for example, lenses 14e.

Optical source 12 emits a tunable optical input beam 16 that is directable onto a predetermined area 22 on a substrate material surface 20 being interrogated. THz source 14 emits a tunable THz input beam 18 that is directable onto a predetermined area 22 on a substrate material surface 20 being interrogated. The optical and THz sources are aligned in a predetermined orientation so that their surface areas of optical illumination overlap at predetermined area 22 on the interrogated substrate material surface 20. This alignment may be implemented via a series of refractive and reflective elements. For example, by changing their tilt in two axes, elements in series can propagate a laser beam to any position on a surface. The optical and THz input beams 16, 18 interact in a predetermined fashion at the predetermined area 22 on substrate material surface 20, such that a combined output signal 24 that is now the sum frequency of the optical and THz source is directed away from the predetermined area 22 on substrate material surface 20. The combined output signal from the optical source 12 and THz source 14 are in the range of from about 0.2 micron to about 1 micron. Sum frequency output 24 is directed to the sum frequency output detector 26. THz second harmonic output 28 is directed to THz second harmonic output detector 30. According to one aspect of this disclosure, the sum frequency detector is a focal plane array that is active in the visible spectrum. The THz sum frequency detector is a single point detector that measures intensity. Detectors in this THz range will typically be bolometers (detectors that collect light, and elevate in temperature, with the thermal response marking the presence of detected and measurable THz radiation).

The optical source 12 includes a visible input in optical communication with associated input optics. The first optical source preferably comprises a narrow frequency bandwidth visible pulse laser, such as, for example a pulsed diode laser, a continuous wave diode laser, a pulsed solid state laser, or a continuous wave solid state laser. Particularly useful lasers are those solid state lasers operating in the range of from about 1 µm to about 250 µm. Such lasers are commercially available from companies including Coherent, SpectraPhysics, etc.

The THz source 14 includes a visible input in optical communication with associated input optics. The input is preferably a narrow frequency bandwidth visible pulse laser, such as, for example a pulsed diode laser, a continuous wave diode laser, a pulsed solid state laser, or a continuous wave solid state laser.

The sum frequency output detector 26 comprises components necessary to receive and process the signals generated as the sum frequency output 24 created by the combined optical source input 16 and THz input 18 that are reflected together from a substrate material surface being interrogated to the detector.

According to one contemplated variation, within the detector 26, signal collection optics receive the combined output from the first and second optical sources that is reflected from the surface being interrogated. A wavelength discriminator or frequency discriminator is positioned between the substrate material and the detection apparatus in detector 26 to insure that the detector 26 receives the signal actually being generated at the substrate material surface without interference occurring through random scattering. The signal collection optics direct the propagation of the sum frequency output so that a collected sum frequency output signal is formed after propagation through the signal collection optics. The signal collection optics may be either refractive or reflective optics that act to control the divergence of the light coming from the surface being interrogated so that as much of the light signal as possible is collected for analysis.

According to a further variation, an optical detector converts the collected optical light signal to an electronic signal, thus monitoring the intensity of the sum frequency output signal as a function of surface characterization. An electronic signal analyzer analyzes the electronic signal for providing surface-sensitive spectroscopic characterizations. According to one aspect, the electronic signal analyzer may be, for example, a computer with suitable internal electronics to implement the appropriate mathematical algorithms to interpret the received electronic signals. The electronic signal analyzer may be located within the detector, may be in communication with the detector, and may be located remotely from the detector but in communication with the detector via known wireless or wired means as would be understood by one skilled in the field.

According to one aspect, the presence of contamination on a surface being interrogated will change the spectroscopic response of the surface. Since the amount of light generated at the sum frequency output wavelength will depend upon the surface spectroscopy, appropriate interpretation of the electronic signal provides a means to monitor the amount of contamination present on the surface.

The THz output detector 30 comprises components necessary to receive, collect and process the signals generated to THz output detector 30, as the THz second harmonic frequency output 28 created by the THz input 18 impacting at and penetrating beneath (penetrating to a preselected depth) the surface of the preselected location 22 interrogating the sub-surface of substrate material 20. According to an aspect of the present disclosure, the THz detector 30 comprises a wavelength discriminator sufficient to reject aspects of the THz input signal, and recognizing only the second harmonic output signal from the substrate material. The THz detector further comprises a polarization control, intensity control and bolometer mentioned above.

According to one contemplated variation, within the THz detector 30, signal collection optics receive the combined output from the first and second optical sources that is reflected from the surface being interrogated. The signal collection optics direct the propagation of the THz second harmonic frequency output so that a THz frequency output signal is formed after propagation through the signal collection optics. The signal collection optics may be either refractive or reflective optics that act to control the divergence of the light coming from the surface being interrogated so that as much of the THZ light signal as possible is collected for analysis. According to a further variation, an optical detector converts the collected optical light signal to an electronic signal, thus monitoring the intensity of the THZ second harmonic frequency output signal as a function of surface characterization. An electronic signal analyzer analyzes the electron signal for providing surface-sensitive spectroscopic characterizations.

According to one aspect, the electronic signal analyzer may comprise, for example, a computer with suitable internal electronics, including appropriate hardware and software, to implement the appropriate mathematical algorithms to interpret the received electronic signals. The electronic signal analyzer may be located within the detector, may be in communication with the detector, and may be located remotely from the detector but in communication with the detector via known wireless or wired means as would be understood by one skilled in the field.

Figure 2:
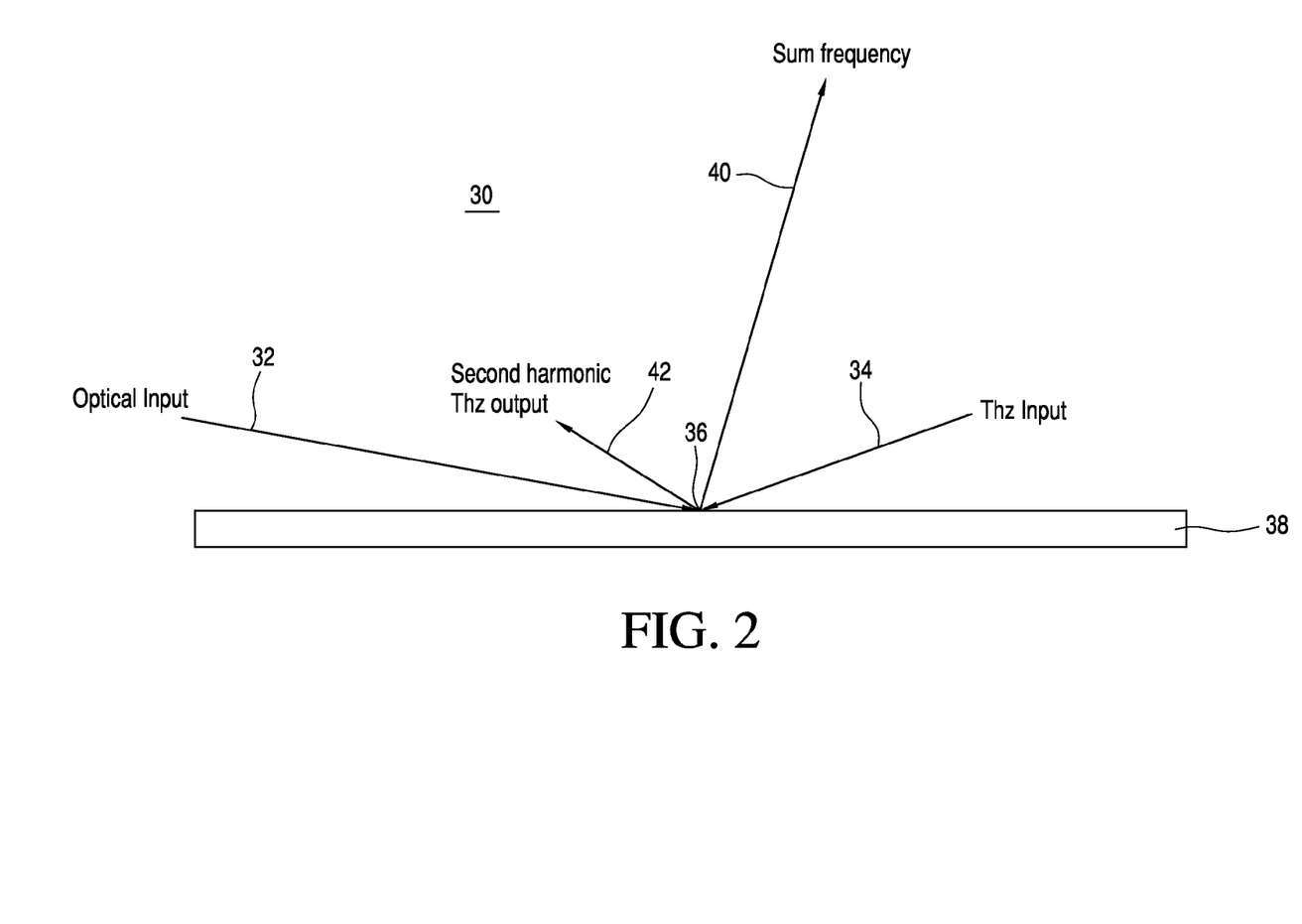
FIG. 2 is a schematic diagram of a variation of the present disclosure.

A further aspect is illustrated in FIG. 2, which shows an alternate positioning of the optical source and the THz source as compared to their orientation as shown in FIG. 1. As shown in FIG. 2, diagnostic system 31 shows a first optical source input 32 from a first optical source (not shown) and a THz source input 34 from a THz source (not shown). As in diagnostic system 10 shown in FIG. 1, the first optical source of diagnostic system 31 comprises a first optical source frequency control, a first optical source intensity control, and a first optical source bandwidth control (all not shown). A THz source of diagnostic system 31 comprises a THz source frequency control, an intensity control, and a bandwidth control (all not shown). Optical source input 32 is a tunable non-THz range input beam that is directable onto a predetermined area 36 on a surface 38 being interrogated. THz source input 34 is a THz range input beam that is directable onto a predetermined area 36 on a surface 38 being interrogated. The inputs 32, 34 are positioned and aligned in a predetermined orientation so that their surface areas of optical illumination overlap on the interrogated surface 38. This alignment may be implemented via a series of refractive and reflective elements. For example, by changing their tilt in two axes, elements in series can propagate a laser beam to any position on a surface. The inputs 32, 34 interact in a predetermined fashion at the predetermined area 36 on surface 38, such that a combined sum frequency signal 40 is directed away from the predetermined area 36 on surface 38. The sum frequency signal from the two inputs is in the range of from about 0.2 micron to about 1 micron. A sum frequency detector (not shown) is positioned to receive, collect and evaluate the sum frequency output signal 40. The inputs 32, 34 also interact in a predetermined fashion at the predetermined area 36 on surface 38, such that a second harmonic THz output frequency signal 42 is directed away from the predetermined area 36 on surface 38. The second harmonic THz output frequency signal from the two inputs is in the range of from about 0.2 to about 200 THz. A THz detector (not shown) is positioned to receive the second harmonic THz output signal 42 from the predetermined area 36 on surface 40.

According to one aspect, the presence of contamination on a surface being interrogated will change the spectroscopic response of the surface. Since the amount of light generated at the THz second harmonic frequency output wavelength will depend upon the substrate material surface and substrate material sub-surface spectroscopy, appropriate interpretation of the electronic signal provides a method for monitoring the amount of contamination present at the substrate material surface and material substrate sub-surface, as well as other characteristics.

According to one aspect, the optical source may comprise a Nd:YAG laser operating on the 1.064 micron line, or a Nd:YAG laser and a harmonic converter for operation at the second or third harmonic of the fundamental output wavelength. It may operate with a maximum pulse length of about 10 nsec, with the optimal pulse length being about 10 psec. According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing output sum frequency wavelength, and a polarizer in optical communication with the filter aligned to detect either the p or s polarization and referenced to the surface where the sum frequency output signal is generated.

According to another aspect of the disclosure, the signal collection optics may include a telescope system comprising a plurality of lenses having desired materials and coatings optimized for the sum frequency output wavelength, in the wavelength band from about 0.2 micron to about 1.0 micron. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

The THz sources that would be required to obtain the detection and detection levels desired, and achieved according to aspects of the present disclosure are not currently commercially available. To achieve the desired effects from a THz source, THz radiation must be produced through parametric oscillation processes or a quantum cascade laser configuration. The parametric oscillator may be constructed with commercially available hardware, but would require on-site installation and customization. Quantum cascade lasers in the THz are under development, but would also require customization and optimization to be useful, and are not yet commercially available for the desired uses described herein. Quantum cascade lasers, as they presently exist, therefore operate only in lower power mode (less than about 1 Watt average power) and therefore cannot operate in the pulsed mode required for non-linear optical mixing contemplated herein. In addition, due to the lack of adequate optical performance, the material properties of quantum cascade lasers cause high material failure rates, rendering them unusable in a manufacturing scenario. Each of these issues must be solved if quantum cascade lasers are to be used in connection with the aspects disclosed herein.

Although the aspects of the present disclosure are useful for all materials regardless of the materials' end uses, material and material surfaces and sub-surfaces interrogated by the methods, systems and apparatuses of the present disclosure are thought to be particularly useful interrogating materials used a components and parts in the manufacture of, for example, manned or unmanned objects and structures in an atmospheric or space environment. Contemplated objects include structures and vehicles, such as, for example, aircraft, satellites, rockets, missiles, etc., and therefor include manned and unmanned aircraft, spacecraft, terrestrial vehicles, non-terrestrial vehicles and even surface and sub-surface water-borne marine vehicles, objects and structures.

Figure 5:
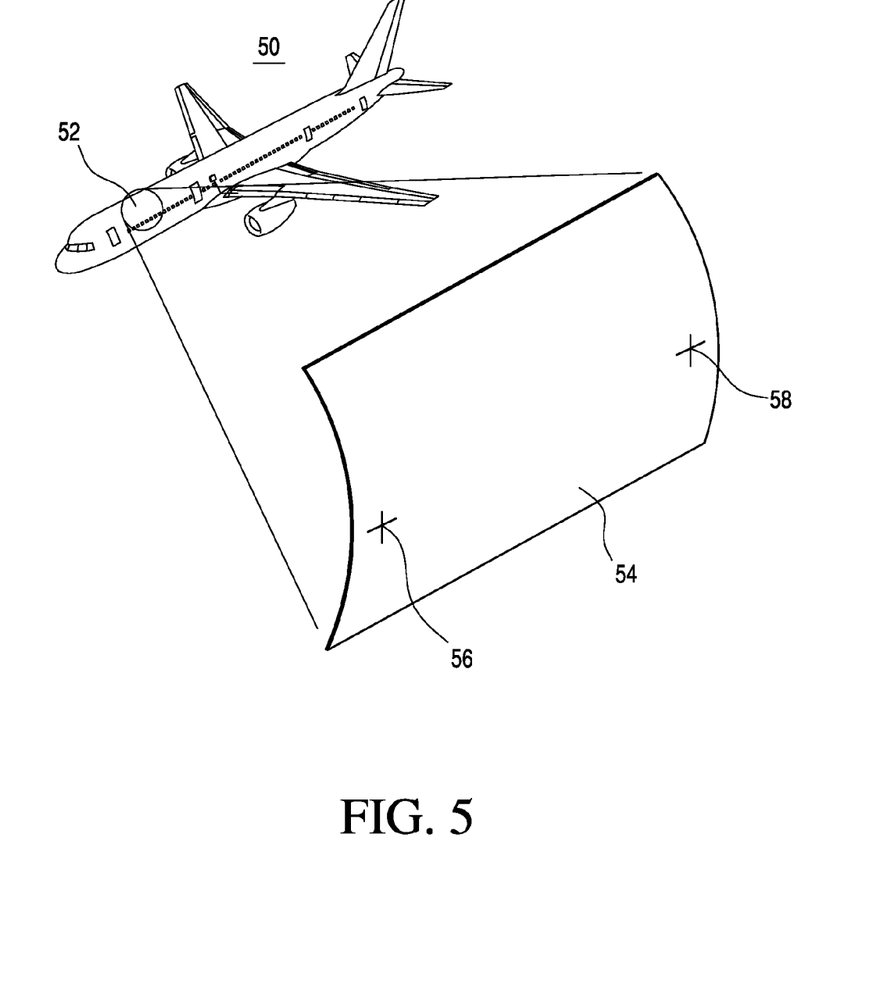
FIG. 5 is a drawing of an aircraft comprising material interrogated by an aspect of the present disclosure.

FIG. 5 is a drawing of a vehicle, and, in particular, an aircraft 50. Fuselage panel 54 having a substrate material surface is shown, in an enlarged configuration, as being located at the region of the fuselage at location 52. The marks shown as "+" 56, 58 represent locations on the substrate material surface and sub-surface of fuselage panel 54 that may be interrogated according to methods, systems and apparatuses of the present disclosure. While the drawing shows an aircraft with a portion of fuselage identified, it is understood that the methods, systems and apparatuses of the present disclosure contemplate use with any material substrate surface of any material that can be used anywhere in the construction of any vehicle, such as, for example an aircraft, including the interior, exterior or locations there between.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

We claim:

1. A method for evaluating a substrate material having a substrate material surface and a substrate material sub-surface comprising the steps of:
   directing a first input beam comprising electromagnetic radiation onto a predetermined area of a substrate material having a substrate material surface and a substrate material sub-surface, the electromagnetic radiation of the first input beam having a wavelength of from about 1000 to about 300 nm;
   directing a second input beam comprising electromagnetic radiation onto the predetermined area of the substrate material surface, the electromagnetic radiation of the second input beam having a THz wavelength between about 0.3 mm and about 3 microns;
   mixing the first input beam and the second input beam at the substrate material surface to provide a sum frequency output beam;
   penetrating the substrate material surface to a predetermined depth of the substrate material sub-surface with the second input beam to provide a THz second harmonic output beam comprising a THz second harmonic signal of the second input beam;
   receiving the sum frequency output beam with a sum frequency output beam detector;
   receiving the THz second harmonic output beam with a THz second harmonic output beam detector; and
   measuring one or more characteristics of the substrate material sub-surface by evaluating the sum frequency output beam received by the sum frequency output beam detector.

2. The method of claim 1, further comprising measuring one or more characteristics of the substrate material surface and the substrate material sub-surface based on the THz second harmonic output beam received by the THz second harmonic output beam detector.

3. The method of claim 1, wherein the substrate material is substantially opaque.

4. The method of claim 1, wherein the second input beam penetrates into the substrate material subsurface surface to a depth of from about 100 microns to about 2 mm beneath the substrate material surface.

5. The method of claim 1, wherein at least one of the first input beam and the second input beam are each emitted from a laser.

6. The method of claim 1, wherein the first input beam and the second input beam are directed onto the predetermined area of the substrate material simultaneously or substantially simultaneously.

7. A system for non-invasively evaluating characteristics of a material surface and a material sub-surface comprising:
   a substrate material having a substrate material surface and a substrate material sub-surface;
   at least one optical source, wherein at least one optical source emits an optical source input beam having a wavelength in the range of from about 1000 nm to about 300 nm;
   at least one THz source, wherein the THz source emits a THz source input beam having a frequency in the THz wavelength range of from about 0.3 mm to about 3 mm;
   at least one sum frequency output detector for detecting a sum frequency output beam produced from combining the optical source input with the THz source input, said detector positioned at a location to receive a sum frequency output beam, said optical source input directed at a predetermined area on the substrate material surface, and said THz source input directed at a predetermined area on the substrate material surface, said sum frequency output reflected from the predetermined area on the substrate material surface to the detector; and
   at least one THz second harmonic frequency output detector for detecting a THz second harmonic frequency output beam from the substrate material surface and substrate material sub-surface, said detector positioned at a location to receive a THz second harmonic frequency output beam, said THz second harmonic frequency output beam reflected from a predetermined area on the substrate material surface and substrate material sub-surface to the THz detector;
   wherein the sum frequency output beam is reflected from the predetermined area on the substrate material surface and substrate material sub-surface, and the sum frequency output beam generates a signal received by the sum frequency detector, and the THz second harmonic frequency output beam is reflected from the predetermined area on the substrate material surface and substrate material sub-surface, and the THz second harmonic frequency output beam generates a signal received by the THz second harmonic frequency detector, with such signals generated substantially simultaneously, with characteristics of the substrate material surface and substrate material sub-surface measured based on the characteristics of the sum frequency output beam received by the sum frequency output detector and the THz second harmonic frequency output received by the THz second harmonic frequency output detector.

8. The system of claim 7, wherein the optical source and the THz source each comprise a laser.

9. The system of claim 7, wherein the THz source emits radiation in a wavelength range of from about 0.3 mm to about 3 microns.

10. The system of claim 7, wherein the THz source having a frequency in the THz frequency range emits radiation that penetrates the substrate material surface.

11. The system of claim 7, wherein the THz source having a frequency in the THz frequency range emits radiation that penetrates into the substrate material sub-surface to a depth of from about 100 microns to about 2.0 mm beneath the substrate material surface.

12. The system of claim 7, wherein at least one sum frequency detector receives a sum frequency output from the substrate material surface and at least one THz detector receives a THz second harmonic frequency output from the substrate material surface and sub-surface.

13. The system of claim 7, wherein at least one detector comprises software to characterize features of the substrate material based on the characteristics of the output beams received by the detector.

14. The system of claim 7, wherein at least one detector generates a signal, and sends the generated signal to a component comprising software to characterize features of the substrate material based on the characteristics of the output beams received by the detector.

15. The system of claim 7, wherein at least one detector generates a signal and sends the generated signal to a remotely located, said remotely located component comprising software to characterize features of the substrate material surface and substrate material sub-surface based on the characteristics of the output beams received by the detector.

16. A vehicle comprising a substrate material surface wherein at least a portion of the substrate material surface is interrogated by:
   directing a first input beam comprising electromagnetic radiation onto a predetermined area of a substrate material having a substrate material surface and a substrate material sub-surface, the electromagnetic radiation of the first input beam having a wavelength of from about 1000 nm to about 300 nm;
   directing a second input beam comprising electromagnetic radiation onto the predetermined area of the substrate material surface, the electromagnetic radiation of the second input beam having a THz wavelength between about 0.3 and about 3 microns;
   mixing the first input beam and the second input beam at the substrate material surface to provide a sum frequency output beam;
   penetrating the substrate material surface to a predetermined depth of the substrate material sub-surface with the second input beam to provide a THz second harmonic output beam comprising a THz second harmonic signal of the second input beam;
   receiving the sum frequency output beam with a sum frequency output beam detector;
   receiving the THz second harmonic output beam with a THz second harmonic output beam detector; and
   measuring one or more characteristics of the substrate material sub-surface by evaluating the sum frequency output beam received by the sum frequency output beam detector.

17. The vehicle of claim 16, wherein the vehicle is an aircraft.

* * * * *